United States Patent
Hahm et al.

(10) Patent No.: US 7,187,754 B2
(45) Date of Patent: Mar. 6, 2007

(54) OPERATING METHOD AND COMPUTER PROGRAM FOR A MEDICAL INSTALLATION

(75) Inventors: Gerhard Hahm, Erlangen (DE); Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 216 days.

(21) Appl. No.: 10/903,346

(22) Filed: Jul. 30, 2004

(65) Prior Publication Data

US 2005/0063511 A1 Mar. 24, 2005

(30) Foreign Application Priority Data

Aug. 1, 2003 (DE) .................................. 103 35 321

(51) Int. Cl.
*H05G 1/64* (2006.01)
*A61B 5/058* (2006.01)
*G01D 18/00* (2006.01)

(52) U.S. Cl. ................. 378/98.7; 378/98.8; 378/98.12; 378/21; 378/207; 600/407; 600/425; 600/473; 600/476; 250/582; 250/583; 250/586

(58) Field of Classification Search ................ 700/17, 700/83, 19, 20, 1; 378/98.7, 19, 21, 98.12, 378/207, 98.8; 358/111; 250/582, 584, 583, 250/581, 586, 591; 600/407, 425, 473, 476

See application file for complete search history.

(56) References Cited

U.S. PATENT DOCUMENTS

| 6,331,885 | B1* | 12/2001 | Nishi ........................... 355/53 |
|---|---|---|---|
| 6,396,074 | B1* | 5/2002 | Tsujii .......................... 250/582 |
| 6,504,895 | B1* | 1/2003 | Dixon et al. ................... 378/19 |
| 6,618,604 | B2 | 9/2003 | Petrick et al. |
| 6,988,012 | B2* | 1/2006 | Renz ............................ 700/81 |
| 2002/0096652 | A1* | 7/2002 | Tsujii .......................... 250/582 |
| 2003/0058985 | A1 | 3/2003 | Renz |
| 2004/0190037 | A1* | 9/2004 | Shindoh ..................... 358/1.13 |
| 2005/0020879 | A1* | 1/2005 | Suzuki ........................ 600/118 |

\* cited by examiner

Primary Examiner—Ramesh Patel
(74) Attorney, Agent, or Firm—Schiff Hardin LLP

(57) ABSTRACT

In an operating method for a medical installation, in particular an x-ray installation. In activation state of the medical installation, a control and evaluation device determines, upon input of a control command, a useful image of a subject. For this purpose, the control and evaluation device receives raw image of the subject acquired by a detector in a first detector mode, and determines the useful image therefrom on the basis of correction data. In a waiting state of the medical installation, the control and evaluation device updates the correction data for the first detector mode repeatedly after the expiration of a basic time interval since the last driving of the detector. For this purpose, the control and evaluation device receives raw data acquired by the detector and uses it to update the correction data. The control and evaluation device updates the correction data for the first detector mode even in the activation state if, since the last updating of the correction data for the first detector mode, at least an additional time interval has elapsed that is greater than the basic time interval.

27 Claims, 5 Drawing Sheets

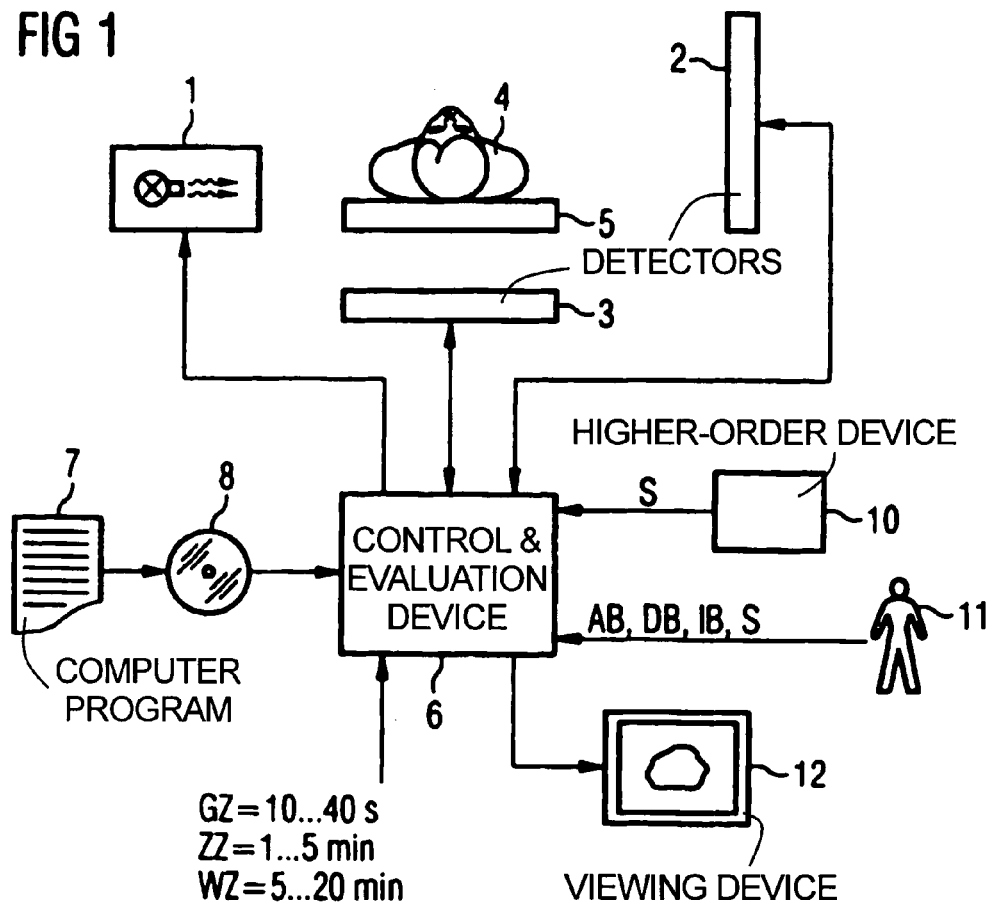
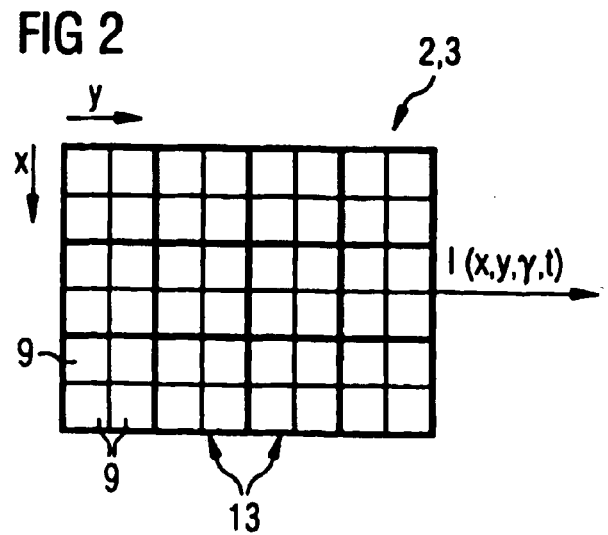

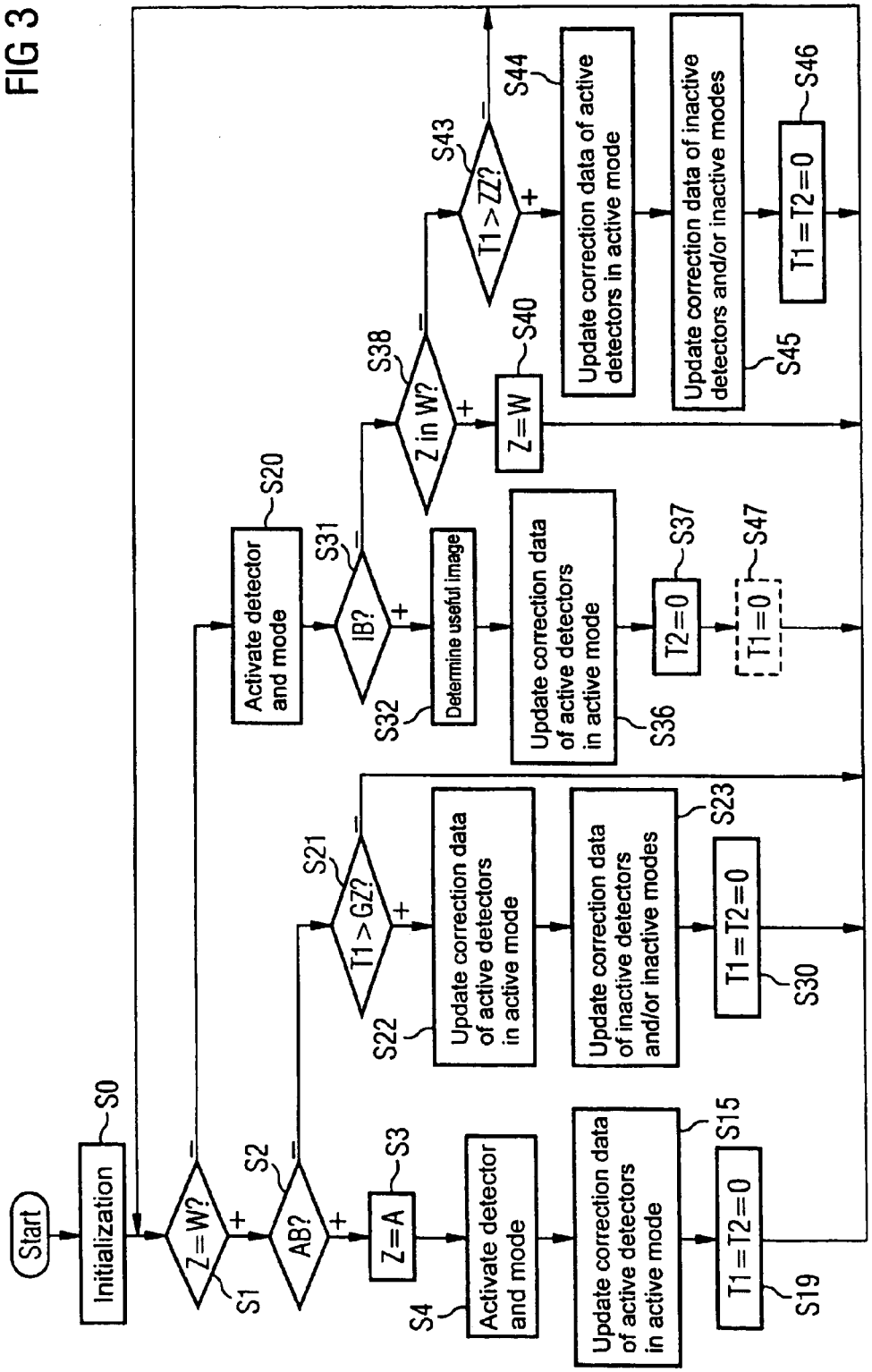

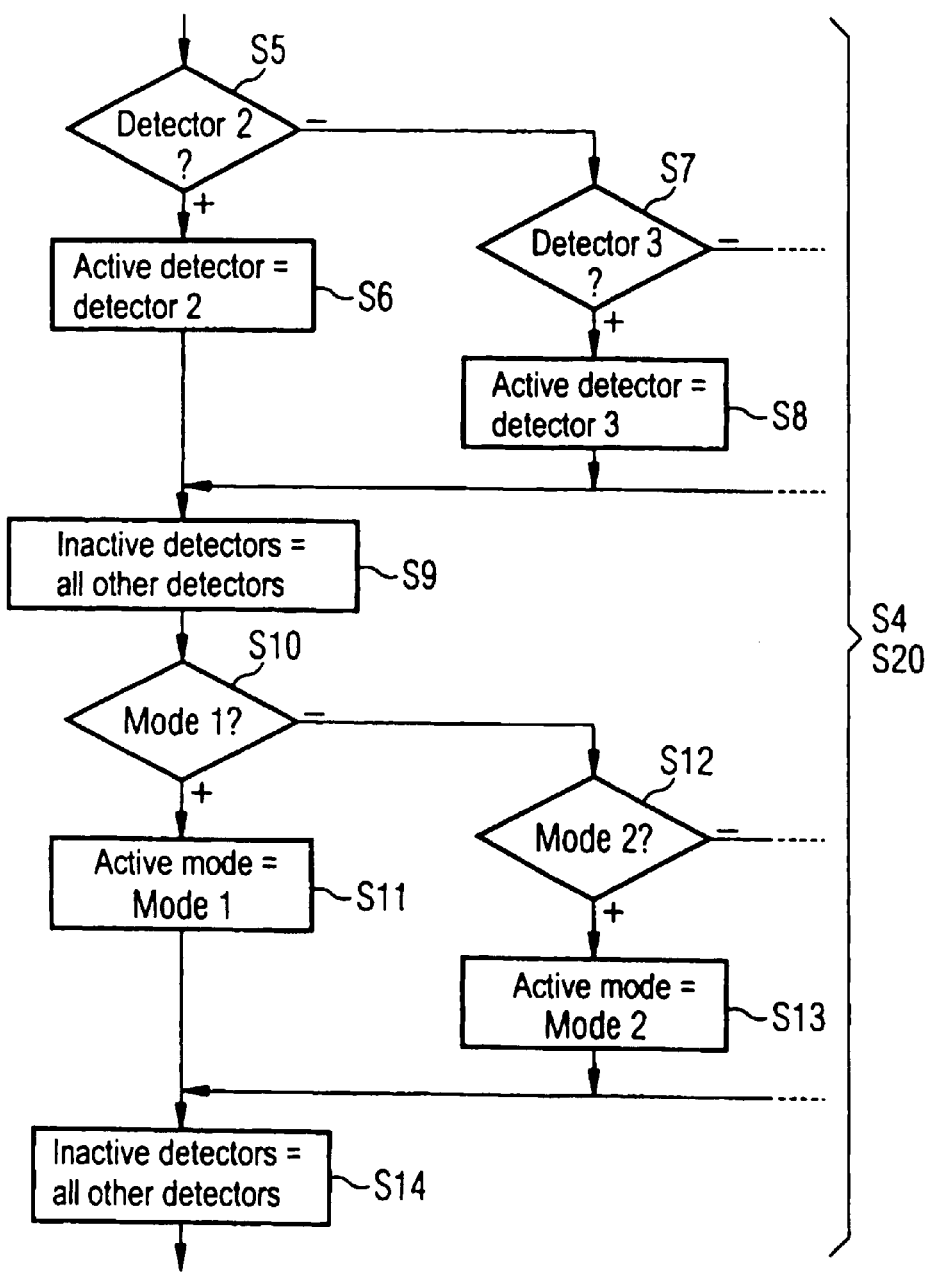

OPERATING METHOD AND COMPUTER PROGRAM FOR A MEDICAL INSTALLATION

BACKGROUND OF THE INVENTION

Field of the Invention

The present invention concerns an operating method for a medical installation, in particular an x-ray installation in addition, the present invention relates to a computer program, stored on a data carrier, for executing such an operating method, a control and evaluation device for a medical installation, in particular an x-ray installation, that can be programmed with such a computer program, and a corresponding medical installation itself.

Operating methods for a medical installation, in particular an x-ray installation, having at least one detector and a control and evaluation device, are known wherein the medical installation is operated in an activated state or in a waiting state. In the activation state, when a control command is entered a control and evaluation device determines a useful image of a subject.

In order to determine a useful image the control and evaluation device drives at least the radiation detector in a first detector mode, so that this detector acquires a rough image of the subject, and acquires rough image from the detector and determines the useful image from the rough image on the basis of correction data for the first detector mode.

In the waiting state the control and evaluation device does not determine any useful images of the subject but, after the expiration of a basic time interval since the last driving of the detector, the control and evaluation device repeatedly updates the correction data for the first detector mode.

For updating the correction data, the control and evaluation device drives at least the detector in the first detector mode, so that this detector acquires raw data, and acquires the raw data from the detector and updates the correction data for the first detector mode on the basis of the raw data.

From German PS 101 46 894, an operating method for a medical installation is known in which the status of at least one element of the installation is acquired automatically by a control device for the installation, and is compared with a reference status. If the comparison fulfills a status condition, the control device initiates a self-test of at least one component of the medical installation. The test result is communicated to the control device and is processed by this device. This document also describes operation of the control device to automatically initiate an immediate interruption of the self-test if, during the self-test, the comparison of the status no longer meets the comparison condition.

In x-ray installations, the increased use of digital x-ray detectors has brought changes in classical radiography, fluoroscopy, angiography, and cardioangiography. These digital technologies include, among others image intensifier camera systems based on television or CCD cameras, storage film systems having an integrated or external readout unit, systems with optical coupling of the converter film to CCDs or CMOS chips, selenium-based detectors with electrostatic readout and solid-state detectors having active readout matrices with direct or indirect conversion of the x-ray radiation.

In particular, for some time there has been development of new solid-state detectors for digital x-ray imaging. In this technology, the detectors are based on active readout matrices, made for example of amorphous silicon. The image information is converted into photons in an x-ray transducer made, for example, of cesium iodide, and is converted into an electrical charge in the photodiodes of the matrix and is stored there. Related technologies likewise use an active readout matrix made of amorphous silicon, but use a transducer that directly generates electrical charge, for example selenium. The charge is then stored on an electrode, and subsequently is read out via an active switching element having a dedicated electronics system, is digitized, and is further processed by the image processing system. Other technologies that supply digital x-ray images are based on CCDs, APS (active pixel sensor), or CMOS chips.

The flat image detectors referred to above have a multiplicity of individual detector elements. The individual detector elements differ from one another. For example, the leakage currents of the photodiode and the switching transistor or switching diode can vary. The same holds, row-by-row or column-by-column, for resistors and capacitors, as well as for amplifier characteristics. In detectors composed of a number of flat image detectors situated alongside one another, different characteristics can in turn occur from one flat image detector to the next.

These are the most basic reasons why the flat image detectors have different properties from pixel to pixel or in their structure (from line to line, from column to column, from detector to detector).

These variations in characteristics have the result that the unprocessed x-ray images cannot be used for the purpose of diagnosis. The images can be further processed using organ-specific image processing software only after a necessary pre-processing of the image, in which the property fluctuations described above are corrected.

The characteristics of the individual detector elements include their sensitivity to x-ray radiation, as well as an offset that is present even in the absence of x-ray radiation. The sensitivity of the detector elements is essentially not dependent on the operating state. It is therefore sufficient to acquire the sensitivity at larger time intervals, for example once per week or per month, and then to take this factor into account in the image processing. The offset, however, is subject to brief non-negligible fluctuations. In particular, it is influenced by temperature, the operating mode, as well as the time elapsed since the changeover from one operating mode to another operating mode. The operating mode includes, for example, a coupling or switching together of detector elements (known as binning), and in particular an integration time that can vary, for example, between 300 ms and five seconds.

All these circumstances, most particularly the integration time, influence the offset. At least the offset therefore must be acquired shortly before the exposure of an x-ray image in order to obtain good useful images.

It is of course conceivable to always carry out an offset acquisition before each x-ray exposure, however, this would result in a significant limitation of the operation of the x-ray installation.

In addition, it is also conceivable to acquire the offset at fixed predetermined intervals (for example, every 30 seconds). Because the offset acquisition lasts several seconds, however, this would have the result that even in continuous operation the medical installation would repeatedly be unavailable for several seconds for x-ray exposures. This would again result in significant limitations in the operation of the installation.

Furthermore, it is conceivable to acquire the offset only when operation is turned on for example only once per day, and to use the offset acquired in this way for the rest of the day as correction data. This would have the result, however, that offset fluctuations during the day would be corrected insufficiently, so that suboptimal useful images would be generated.

SUMMARY OF THE INVENTION

An object of the present invention is to provide an operating method for a medical installation of the initially described type wherein the useful operation of the medical installation is limited as little as possible, and wherein the correction data that are to be taken into account (that is, at least the offset of the detector elements, and possibly also their sensitivities) are kept very up-to-date with certainty or at least with a high degree of probability.

Based on an operating method of the type described above, this object is achieved by the control and evaluation device updating the correction data for the first detector mode even in the activation state, if, since the last updating of the correction data for the first detector mode, at least an additional time interval has elapsed that is greater than the basic time interval.

For example, it is possible that in the activation state the control and evaluation device always updates the correction data for the first detector mode whenever the additional time interval has elapsed since the last updating of the correction data for the first detector mode. In this case, the correction data for the first detector mode are updated in every case, but there is a slight influence on the availability of the medical installation.

Alternatively, it is also possible that in the activation state the control and evaluation device updates the correction data for the first detector mode only if the additional time interval has elapsed since the last driving of the detector in the first detector mode. In this case, the influence on the availability of the medical installation is completely negligible. However, if there is a rapid sequence of useful images that are to be determined, it may occur that the correction data for the first detector mode become obsolete.

The additional time interval should be at least five times, and in particular five to ten times, as large as the basic time interval. For example, the basic time interval can be between 10 and 40 seconds, and in particular can be approximately 20 seconds, while the additional time interval can be between one and five minutes, in particular approximately two minutes.

If the control and evaluation device again updates the correction data for the first detector mode when the medical installation changes from the waiting state to the activation state, the correction data for the first detector mode are kept as current as possible without any appreciable influence on the availability of the medical installation.

In an embodiment wherein in the updating state and immediately following the determination of a useful image, the control and evaluation device updates correction data of at least one additional detector that is not driven for this useful image, at least the correction data of the additional detector or detectors are kept up-to-date without any influence on the availability of the medical installation.

Analogously, if the detector can also be driven in at least one second detector mode and the correction data are mode-specific, it is also possible for the control and evaluation device, in the activation state and immediately following the determination of a useful image in the first detector mode, to update the correction data for the second detector mode.

In an embodiment wherein for the determination of a useful image, the control and evaluation device drives a radiation source in addition to driving the detector, and does not drive the radiation source for the determination of the correction data, a pure offset determination takes place. In principle, however, it would also be possible to drive the radiation source for the determination of the correction data as well, for example in order to determine the complete sensitivity characteristic curves of the individual detector elements.

In an embodiment wherein the medical installation automatically goes into the activation state when it is given an activation command by a higher-order device, for example an RIS (radiology information system), or by a person operating the installation, the system operates in a particularly easy-to-use fashion.

In an embodiment wherein the medical installation is given a predetermined image sequence that is to be produced using the medical installation, and the medical installation remains in the activation state until the image sequence has been completely processed, the operating method works even better.

In an embodiment wherein the medical installation goes into the wait state if a deactivation command is given, for example by an operator, the correction data are updated again as soon as possible.

In an embodiment wherein the medical installation goes into the wait state if a waiting period has elapsed since the last determination of a useful image that is greater than the basic time interval, the medical installation then goes back into the wait state even if an active switching back into the wait state has accidentally been omitted. The wait time preferably is greater than the additional time interval, in particular at least three times as long. For example, it can be between five and twenty minutes, for example approximately ten minutes.

DESCRIPTION OF THE DRAWINGS

FIG. 1 is a schematic illustration of a medical installation operable in accordance with the inventive method.

FIG. 2 is a top view of a detector useable in the installation of FIG. 1.

FIGS. 3 to 8 are flowcharts of various embodiments of the inventive method.

DESCRIPTION OF THE PREFERRED EMBODIMENTS

Figure 5:
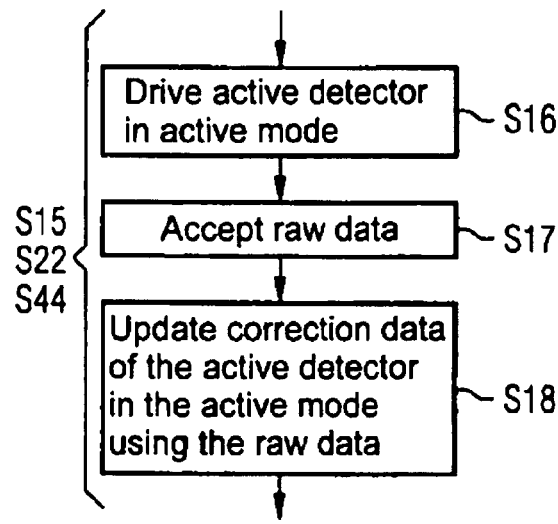

As shown in FIG. 1, a medical installation is formed, as an example, as an x-ray installation. The x-ray installation has an x-ray source 1 and a number (here, two) of detectors 2, 3. Using detectors 2, 3, it is possible to acquire images of an examination subject 4, for example a person. The examination subject 4 can be situated, for example, on a patient support platform 5 for this purpose.

The x-ray installation also has a control and evaluation device 6. The control and evaluation device 6 is programmed with a computer program 7 that is stored in (exclusively) machine-readable form on a data carrier 8, for example a CD-ROM 8, and is supplied to the control and evaluation device 6 via a data carrier 8. On the basis of the programming with the computer program 7, the control and evaluation device 6 operates the medical installation in a manner that is described in more detail below in connection with FIGS. 3 and 4.

First, however, it should be noted that detectors 2, 3 according to FIG. 2 are surface detectors having a multiplicity of detector elements 9. Upon irradiation of the detector 2, 3 with x-ray radiation, each detector element 9 supplies a signal I that depends on a radiation intensity y and a number of additional factors, including the sensitivity of the respective detector element 9 and an integration time t. In addition to its radiation-dependent portion, the signal I also exhibits an offset that is present even when the detector element 9 is not exposed to x-ray radiation.

The detectors 2, 3 can often be operated in more than one detector mode. In particular, each integration time corresponds to a separate detector mode. Furthermore, it is alternatively or additionally possible for a number of detector elements 9 to be capable of being coupled together to form a macroelement 13 (in this example composed of four detector elements 9). Such macroelements 13 can have characteristics that are not necessarily correlated with those of the individual detector elements 9.

The correction data must be acquired, stored, and used for the determination of the useful images in mode-specific fashion.

The sensitivity is dependent to a small extent on the operating conditions (e.g., the ambient temperature) of detector elements 9. In contrast, the offset is dependent on the operating conditions to a large extent. For this reason, at least the offset must be constantly redetermined, and this must be done for each individual detector element 9, in order to enable useful images of the examination subject 4 to be obtained.

In the following, in connection with FIGS. 3 to 8 it is described only how the offset is updated, or kept up-to-date. In principle, however, the procedure described in connection with FIGS. 3 to 8 also can be applied to the acquisition of further correction data, in particular for determining the sensitivity.

According to FIG. 3, first a step S0 is carried out in which the x-ray installation is initialized. For example, the state Z of the installation can be set to a waiting state W, and a time interval T1 can be set equal to a basic time interval GZ. The basic time interval GZ can be given to the control and evaluation device 6 for example externally, such as using the higher-order device 10, or by an operator 11, or in some other way. The basic time interval GZ (see FIG. 1) Is preferably between 10 and 40 seconds, e.g. approximately 20 seconds.

Next, in a step S1 the control and evaluation device 6 tests whether the current state Z of the medical installation is an activation state A or is waiting state W. If the medical installation is in waiting state W, a step S2 is next carried out in which the control and evaluation device 6 checks whether it has been given an activation command AB. This command can, for example, given by an operator 11 (see FIG. 1). Alternatively, the control and evaluation device 6 can itself derive activation command AB from other inputs from a higher-order device 10, e.g. an RIS. This can also be regarded as an input made by the higher-order device 10.

If the control and evaluation device 6 has been given an activation command AB, then in a step S3 the control and evaluation device 6 changes state Z to activation state A. It then executes a step S4. In step S4, the control and evaluation device 6 activates one of the detectors 2, 3 in a first detector mode. Step 84 is thereby subdivided into a number of steps S5 to S14, which are explained in more detail below in connection with FIG. 4.

According to FIG. 4, in step S5 the control and evaluation device 6 checks whether detector 2 is supposed to be the active detector. If the result is yes, this is set in step S6.

Otherwise, the control and evaluation device 6 branches to step S7, where it checks whether detector 3 is supposed to be the active detector. If this is the case, in step S8 it sets detector 3 as the active detector.

If more than two detectors 2, 3 are present, the additional detectors 2, 3 are progressively tested until it has been determined which detector 2, 3 is the active detector.

After the determination of the active detector, in step S9 all other detectors 2, 3 are switched inactive. The sequence of steps 85 to S9 thus has the result that one of the detectors 2, 3, e.g. detector 2, is activated, and the others are inactive.

As explained above, the detectors 2, 3 can be operated in various detector modes. Analogous to the determination of the active detector 2, 3, in steps 10 to 14 the active mode is determined for the active detector (e.g., detector 2), and all other modes are deactivated. Steps S10 to S14 are thereby constructed analogously to steps S5 to S9, so that a detailed explanation is omitted here.

A step S15 is then carded out (see again FIG. 3). In step S15, the control and evaluation device 6 updates correction data of the active detector 2, 3 in the active detector mode. Step S15 is also subdivided into a number of steps S16 to S19, which are explained in more detail below in connection with FIG. 5.

According to FIG. 5, in a step S16 the control and evaluation device 6 drives whichever of detectors 2, 3 is active, e.g. detector 2, in the active mode, so that this detector acquires raw data. The x-ray source 1 is not driven. In this case, the raw data therefore correspond to the offsets. In a step S17, the control and evaluation device 6 receives the raw data acquired by detector 2 and then, in a step S18, updates, on the basis of the communicated raw data, the correction data of active detector 2, 3 in the active mode.

According to FIG. 3, in a step S19 the control and evaluation device 6 then sets the time T1, as well as an additional time T2, to the value zero. After step S19 has been carried out, the control and evaluation device 6 again branches to step S1. However, because in the meantime the state Z was changed to the activation state, branching now takes place from step S1 to a step 320.

Step S20 is discussed again later in connection with updating state A. However, here it can already be seen that the sequence of steps S2 to S19 has in particular the effect that when there is a change of the medical installation from waiting state W to activation state A, the control and evaluation device 6 again updates the correction data of the active detector 2, 3 in the active detector mode.

If no activation command AB has been given to the control and evaluation device 6, this device branches from step S2 to a step S21. In this step S21, the control and evaluation device 6 checks whether time T1 has exceeded the basic time interval GZ.

As long as time T1 has not yet exceeded basic time interval GZ, the control and evaluation device 6 goes back to step S1. If, on the other hand, the basic time interval GZ has been exceeded, the control and evaluation device 6 branches to a step S22. Step S22 corresponds to step 815, so that a detailed explanation of step S22 is omitted in order to avoid repetition.

After step S22, the control and evaluation device 6 carries out a step S23. In step S23, the control and evaluation device 6 updates correction data of the inactive detectors 2, 3 and/or correction data of the active detector 2, 3 in inactive modes.

Step S23 is subdivided for example into a number of steps S24 to 829, which are explained in more detail below in connection with FIG. 6.

Figure 6:
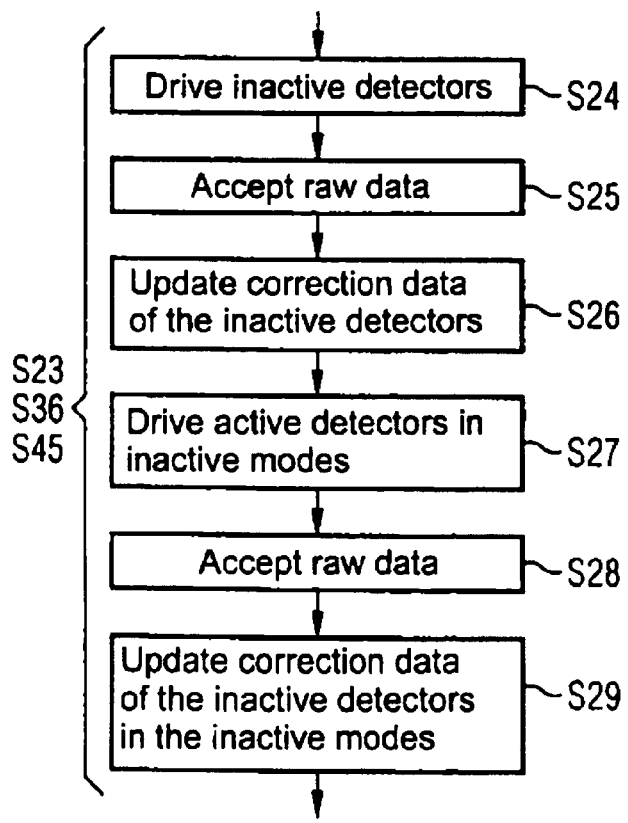

According to FIG. 6, in step S24 the control and evaluation device 6 first drives inactive detector or detectors 3. The x-ray source 1 remains undriven. Due to the driving, inactive detector 3 acquires raw data that are received by the control and evaluation device 6 in step S25. In step S26, the control and evaluation device 6 then updates the correction date of inactive detector or detectors 3.

Steps S24 to S26 are carried out at least in the same mode that is activated with respect to the active detector 2. If necessary, they can additionally be carried out in the modes in which active detector 2 is not activated.

Subsequently, in step S27 the control and evaluation device 6 drives active detector 2 in its inactive mode or in its inactive modes. In step S27 as well, the x-ray source 1 remains undriven. The active detector 2 therefore acquires raw data that are again received by the control and evaluation device 6 in step S28. In step S29, the control and evaluation device 6 then updates the correction data of the active detector 2 in its inactive mode or in its inactive modes.

After step S29, a step S30 Is then carried out (see again FIG. 3). Step S30 corresponds to step S19. In step S30, times T1 and T2 are thus again reset.

This sequence of commands thus has the effect that in the waiting state W the control and evaluation device 6 repeatedly updates the correction data of all detectors 2, 3 in all modes after the basic time period GZ since the last driving of the respective detector 2, 3 has elapsed.

If the medical installation is in activation state A, the control and evaluation device 6 branches from step S1 to step S20, as was already mentioned above. Step S20 corresponds to step S4, so that a detailed explanation of step S20 is omitted below in order to avoid repetition.

In the processing of step S20 immediately after the transition to activated state A, that is, during the execution of the sequence of steps S1-S2-S3-S4-S15-S19-S1-S20, the processing of step S20 remains without influence, However, on the basis of step S20 it is possible to change the active detector 2, 3 and/or the active detector mode, even in activation state A.

After step S20, the control and evaluation device 6 executes a step S31. In step S31, the control and evaluation device 6 checks whether it has been given a recording command IB for recording and determining a useful image. Generally, this command IB is given to control and evaluation device 6 by operator 11. If the recording command IB has been given, the control and evaluation device 6 executes a step S32 in which it determines a useful image.

Figure 7:
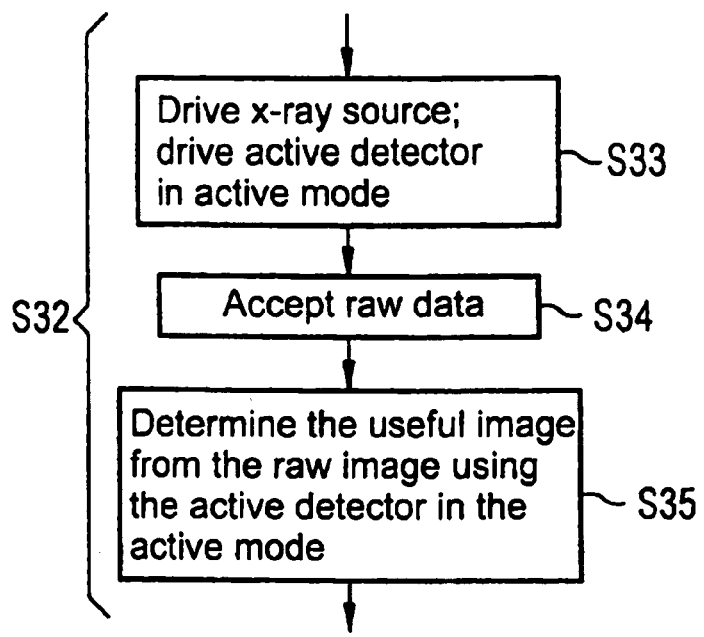
Figure 8:
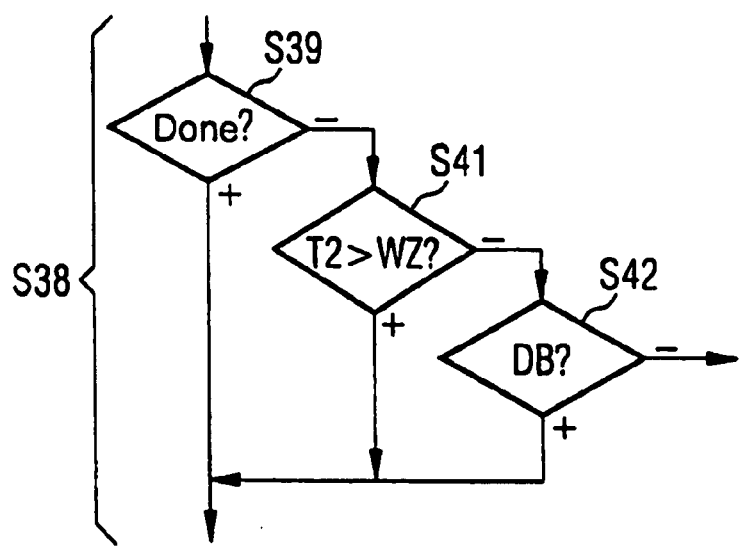

According to FIG. 7, step S32 is subdivided into steps 333 to 835. In step S33, the control and evaluation device 6 first drives, in the active detector mode, the active detector 2, 3 (here e.g. again detector 2) as well as the x-ray source 1, so that driven detector 2, 3 acquires, in the active detector mode, a raw image of subject 4. In step S34, the control and evaluation device 6 then takes over the acquired raw image from active detector 2, and in step S35 determines the useful image from the raw image on the basis of the correction data of active detector 2 for the active detector mode. The useful image can be output to operator 11 by the control and evaluation device 6, for example via a viewing device 12. However, arbitrary different ways of handling the useful image are also possible, for example a storing or archiving of the image, or forwarding of the image to the higher-order device 10.

The determination of the useful image in step S32 takes place with the active detector 2, 3 in the active detector mode. After step S32, the control and evaluation device 6 therefore executes a step S36. In step S36, control and evaluation device 6 again updates the correction data of the inactive detectors 3 and/or of the active detector 2 in the inactive modes. The updating of the correction data thereby takes place in a manner analogous to step S23, so that detailed explanations are omitted here.

In a step S37, time T2 is then reset, and from there branching to step S1 takes place.

The useful images are not determined continuously. Rather, there are pauses between the determination of the useful images, for example in order to position the examination subject 4 differently, to orient the x-ray source 1 differently, to activate a different detector 2, 3, or for other reasons. In all these cases a branching from step S31 to step S38 takes place, because at this point in time no recording command IB is present.

In step S38, the control and evaluation device 6 checks whether activation state A should be left. Step S38 is subdivided into a number of steps S39, S41, and S42, This is explained in more detail below in connection with FIG. 8.

Thus, it is for example possible to give the control and evaluation device 6 a sequence S of useful images to be determined that are to be produced using the medical installation. In this case, the control and evaluation device 6 checks in step S39 whether the sequence S has already been completely produced. Only if the sequence S has been completely produced, the control and evaluation device 6 branches to a step S40, in which it changes the state Z of the medical installation to the wait state W. Otherwise, it branches to step S41. It thus remains, at least as a rule, in activation state A until the sequence S has been completely executed.

In step S41, control and evaluation device B checks whether time T2 has exceeded a w the waiting time WZ. If this is the case, the control and evaluation device 6 likewise branches to step S40. Analogously to the basic time interval GZ, waiting time WZ can be fixedly predetermined or can be given to control and evaluation device 6 externally. However, the waiting time WZ is always longer than the basic time interval GZ. Preferably, it is between five and 20 minutes, e.g. approximately 10 minutes.

If the time T2 has not yet exceeded the waiting time WZ, control and evaluation device 6 branches to step S42. In step S42, the control and evaluation device 6 checks whether it has been given a deactivation command DB, for example by operator 11. If this is the case, it again branches to step S40; otherwise, it executes a step S43.

In step S43, the control and evaluation device 6 checks whether the time T1 has exceeded an additional time interval ZZ. If this is the case, it branches to steps S44 to S46; otherwise, it branches to step S1.

In step S44, the control and evaluation device 6 updates the correction data of the active detector 2 in the active detector mode. In step S45, it updates the correction data of the inactive detectors 3, and/or in the inactive modes it also updates the correction data of the active detector 2. In step S46, it resets the times T1 and T2. Steps S44 to S46 thus correspond to the steps S22, S23, and S30. In order to avoid repetitions, reference is therefore made to the explanations of these steps S22, S23, and S30. However, it should be noted that on the basis of steps 843 to S46 an updating of the correction data of detectors 2, 3 in all operating modes, and in particular also of the active detector 2 for the active detector mode, takes place even in the activation state A if at least the additional time interval ZZ has elapsed since the last updating of the correction data of the active detector 2 for the active mode.

Like the basic time interval GZ and the waiting time WZ, the additional time interval ZZ can be fixedly predetermined or can be inputted externally. It is preferably at least five times as large, in particular five to 10 times as large, as basic the time interval GZ. For example, it can be between one and five minutes, in particular approximately two minutes, It is thus in particular greater than the basic time interval GZ, but is smaller than waiting time WZ. Preferably, the additional time interval ZZ is between ⅙ and ⅓ of the waiting time WZ.

In the procedure described in connection with FIGS. 3 to 8, in the updating state A the control and evaluation device 6 always updates the correction data when the additional time interval ZZ since the last updating of the correction data has elapsed. However, the operating method according to the present invention can be modified, as is shown in FIG. 3 in broken lines, by means of a step S47 that follows step S37.

In step S47, the control and evaluation device 6 sets the time T1 to zero. If step S47 is added, the operating method according to the present invention is thus modified in such a way that in the activation state A the control and evaluation device 6 updates the correction data only if the additional time interval ZZ has elapsed since the last driving of detector 2. This thus holds independent of whether the last driving of active detector 2 took place in the context of steps S15, S22 or S44, or in the context of step S32.

The procedure according to the present invention results in only an extremely slight adverse effect on the availability of the medical installation, while the correction data are kept very up-to-date with certainty or at least with a high degree of probability.

Although modifications and changes may be suggested by those skilled in the art, it is the intention of the inventors to embody within the patent warranted hereon all changes and modifications as reasonably and properly come within the scope of their contribution to the art.

We claim as our invention:

1. An operating method for a medical installation for obtaining images of a subject, having at least one image detector and a control and evaluation device connected thereto, comprising the steps of:

selectively operating said medical installation in an activation state or in a waiting state, said waiting state following each activation state;

in said activation state, entering a control command to said control and evaluation device for causing said control and evaluation device to operate said medical installation to obtain an image of a subject, including driving said image detector in a detector mode to cause said image detector to acquire a raw image of the subject, said control and evaluation device receiving said raw image from said image detector and determining a useful image from said raw image on the basis of a correction data image for said detector mode;

in said waiting state, acquiring no useful image in said control and evaluation device and, after expiration of a basic time interval since a last driving of said image detector in an immediately preceding activation state, in said control and evaluation device updating said correction data image for said detector mode;

for updating said correction data image, said control and evaluation device driving said image detector in said detector mode to cause said image detector to acquire am further raw data image, and receiving said further raw image in said control and evaluation device from said image detector and updating said correction data image for said detector mode based on said image raw image in said control and evaluation device; and in said control and evaluation device, additionally updating said correction data image for said detector mode in said activation state if an additional time interval greater than said basic time interval, has elapsed since a last updating of said correction data image.

2. An operating method as claimed in claim 1 comprising:

in said activation state, in said control and evaluation device always updating said correction data image for said detector mode if said additional time interval has elapsed since said last updating of said correction data image.

3. An operating method as claimed in claim 1 comprising:

in said activation state, in said control and evaluation device updating said correction data image for said detector mode only if said additional time interval has elapsed since said last driving of said image detector in said detector mode.

4. An operating method as claimed in claim 1 comprising employing a time interval as said additional time interval that is at least five times as large as said basic time interval.

5. An operating method as claimed in claim 4 comprising employing a time interval as said additional time interval that is up to ten times as large as said basic time interval.

6. An operating method as claimed in claim 1 comprising employing a time interval as said basic time interval that is between ten and forty seconds.

7. An operating method as claimed in claim 1 comprising employing a time interval as said basic time interval that is approximately twenty seconds.

8. An operating method as claimed in claim 1 comprising employing a time interval as said additional time interval that is between one and five minutes.

9. An operating method as claimed in claim 1 comprising employing a time interval as said additional time interval that is approximately two minutes.

10. An operating method as claimed in claim 1 comprising:

in said control and evaluation device, updating said correction data image for said detector mode when said medical installation changes operation from said waiting state to said activation state.

11. An operating method as claimed in claim 1 wherein said image detector is a first image detector and wherein said medical installation comprises a second image detector, and wherein only said first image detector is driven for obtaining said raw image for determining said useful image, and comprising:

in said activation state, in said control and evaluation device updating, immediately following determination of said useful image, a correction data image for said second image detector.

12. An operating method as claimed in claim 1 wherein said detector mode is a first detector mode and wherein said image detector is also drivable in a second detector mode, and comprising:

selectively driving said image detector in one of said first detector mode and said second detector mode to obtain said raw image; and in said control and evaluation device, determining said useful image from said raw image based on a correction data image that is specific for the detector mode in which said image detector was driven for obtaining said raw image.

13. An operating method as claimed in claim 1 wherein said medical installation has a radiation source connected to said control and evaluation device, and comprising:
   in addition to driving said image detector for obtaining said raw image, driving said radiation source by said control and evaluation device; and
   not driving said radiation source by said control and evaluation device for determining said correction data image.

14. An operating method as claimed in claim 1 comprising automatically switching said medical installation into said activation state upon entry of an activation command into said control and evaluation device.

15. An operating method as claimed in claim 14 comprising supplying said activation command from a higher-order device.

16. An operating method as claimed in claim 15 comprising supplying said activation command from an RIS, as said higher-order device.

17. An operating method as claimed in claim 14 comprising supplying said activation command as a manual input from an operator.

18. An operating method as claimed in claim 14 comprising:
   producing a sequence of useful images of the subject in said medical installation by successively driving said image detector in said activation state, and maintaining said medical installation in said activation state until said image sequence is completed.

19. An operating method as claimed in claim 1 comprising switching said medical installation into said waiting state by entering a deactivation command into said control and evaluation device.

20. An operating method as claimed in claim 19 comprising supplying said deactivation command as a manual input from an operator.

21. An operating method as claimed in claim 1 comprising automatically switching said medical installation into said waiting state if, since a last determination of said useful image, a waiting time has elapsed that is longer than said basic time interval.

22. An operating method as claimed in claim 21 comprising employing a time as said waiting time that is greater than said additional time interval.

23. An operating method as claimed in claim 21 comprising employing a time as said waiting time that is at least three times as large as said additional time interval.

24. An operating method as claimed in claim 21 comprising employing a time as said waiting time that is between five and twenty minutes.

25. An operating method as claimed in claim 21 comprising employing a time as said waiting time that is approximately ten minutes.

26. A computer-readable medium encodes with a data structure for operating a medical installation for obtaining images of a subject, having at least one image detector and a control and evaluation device connected thereto into which said computer-readable medium is loaded for causing said control and evaluation device to:
   selectively operate said medical installation in an activation state or in a waiting state, said waiting state following each activations state;
   in said activation state, respond to a control command entered into said control and evaluation device to operate said medical installation to obtain an image of a subject, including driving said image detector in a detector mode and causing said image detector to acquire a raw image of the subject, and receive said raw image from said image detector and determine a useful image from said raw image on the basis of a correction data image for said detector mode;
   in said waiting state, acquire no useful image and, after expiration of a basic time interval since a last driving of said image detector, update said correction data image for said detector mode;
   for updating said correction data image, drive said image detector in said detector mode to cause said image detector to acquire a further raw image, and receive said further raw image in said control and evaluation device from said image detector and to update said correction data image for said detector mode based on said further raw image; and
   additionally update said correction data image for said detector mode in said activation state if an additional time interval greater than said basic time interval, has elapsed since a last updating of said correction data image.

27. A medical installation comprising:
   a radiation source that emits radiation;
   at least one image detector disposed with respect to said radiation source and adapted to allow an examination subject to be positioned between said radiation source and said image detector, for detecting said radiation from said radiation source attenuated by said examination subject; and
   a control and evaluation device connected to said radiation source and to said image detector, for selectively operating said medical installation in an activation state or in a waiting state, with said waiting state following each activation state, and for, in said activation state, entering a control command to said control and evaluation device for causing said control and evaluation device to operate said medical installation to obtain an image of a subject, including driving said image detector in a first detector mode to cause said image detector to acquire a raw image of the subject, and for receiving said raw image from said image detector and determining a useful image from said raw image on the basis of a correction data image for said detector mode, and for, in said waiting state, acquiring no useful image in said control and evaluation device and for, after expiration of a basic time interval since a last driving of said image detector, updating said correction data image for said detector mode by driving said image detector in said first detector mode to cause said image detector to acquire a further raw image and receiving said further raw data image in said control and evaluation device from said image detector and updating said correction data image for said detector mode based on said raw data in said control and evaluation device, and for additionally updating said correction data for said first detector mode in said activation state if an additional time interval greater than said basic time interval, has elapsed since a last updating of said correction data image.

* * * * *